United States Patent [19]
Kleefstra

[11] Patent Number: 4,546,488
[45] Date of Patent: Oct. 8, 1985

[54] X-RAY ANALYSIS APPARATUS WITH PULSE AMPLITUDE SHIFT CORRECTION

[75] Inventor: Meindert J. Kleefstra, Prairieview, Ill.

[73] Assignee: U.S. Philips Corporation, New York, N.Y.

[21] Appl. No.: 480,548

[22] Filed: Mar. 30, 1983

[30] Foreign Application Priority Data

Mar. 31, 1982 [NL] Netherlands ............ 8201342

[51] Int. Cl.$^4$ .................. G01N 23/20; G01T 1/17
[52] U.S. Cl. ................................. 378/49; 378/84
[58] Field of Search .............. 378/49, 83, 48, 47, 378/84

[56] References Cited

U.S. PATENT DOCUMENTS

| 2,837,655 | 6/1958 | Lang | 378/49 |
| 3,790,792 | 2/1974 | Ishijima | 378/49 |
| 4,352,288 | 10/1982 | Paap et al. | 378/47 |

Primary Examiner—Alfred E. Smith
Assistant Examiner—T. N. Grigsby
Attorney, Agent, or Firm—Paul R. Miller

[57] ABSTRACT

In an X-ray analysis apparatus, a pulse amplitude shift correction circuit is provided for producing correction signals which are a measure of pulse amplitude shifts and which are in response to the pulse amplitude shifts. This circuit provides automatic correction of pulse amplitude shifts so that the pulse amplifier of the device is controlled.

4 Claims, 3 Drawing Figures

X-RAY ANALYSIS APPARATUS WITH PULSE AMPLITUDE SHIFT CORRECTION

The invention relates to an X-ray analysis apparatus having an X-ray source, a sample holder and an X-ray detector with a pulse amplifier and a pulse counter.

Such an apparatus is known in the form of an X-ray fluorescence apparatus from U.S. Pat. No. 3,119,013. In such apparatus, pulse amplitude shifts may lead to the occurrence of measurement errors which will adversely affect the accuracy of the analysis. Such pulse amplitude shifts are mainly due to variations in the natural amplification of the X-ray gas ionisation detector used, but can also result from thermal drift.

The invention has for its object to provide an automatic correction of such pulse amplitude shifts. According to the invention, an X-ray analysis apparatus of the kind mentioned in the opening paragraph is therefore characterized in that the pulse amplifier is controlled by a correction voltage which is provided by a pulse comparison circuit as a measure of and in response to the occurrence of pulse amplitude shifts.

When the amplification of the pulse amplifier is readjusted by a correction voltage related to the extent of the pulse amplitude shift, in apparatus according to the invention, the pulses to be measured are restored to their correct value. Thus, it is possible to measure more accurately or on the other hand variations in the natural amplification of the gas ionisation detector may be reduced or prevented.

In a preferred embodiment, the pulse amplitude shift correction circuit comprises three parallel connected amplitude discriminators, two window circuits connected thereto and a comparator connected thereto, which is provided with an analogue memory, a control circuit and a feed-back connection. It is then favourable to add to each window circuit a rate meter, each of these meters converting the count rate in the corresponding channel into an analogue voltage. In the comparator, these analogue voltages are compared with each other. When the voltages are unequal, a voltage variation is produced which as a control signal for the control part of an output voltage thereof is fed back to the controllable amplifier, as a result of which the amplification thereof is readjusted. By this control, the pulse peak is shifted back to a position fixed therefor.

An embodiment according to the invention will now be described with reference to the drawing. In the drawing.

Figure 1:
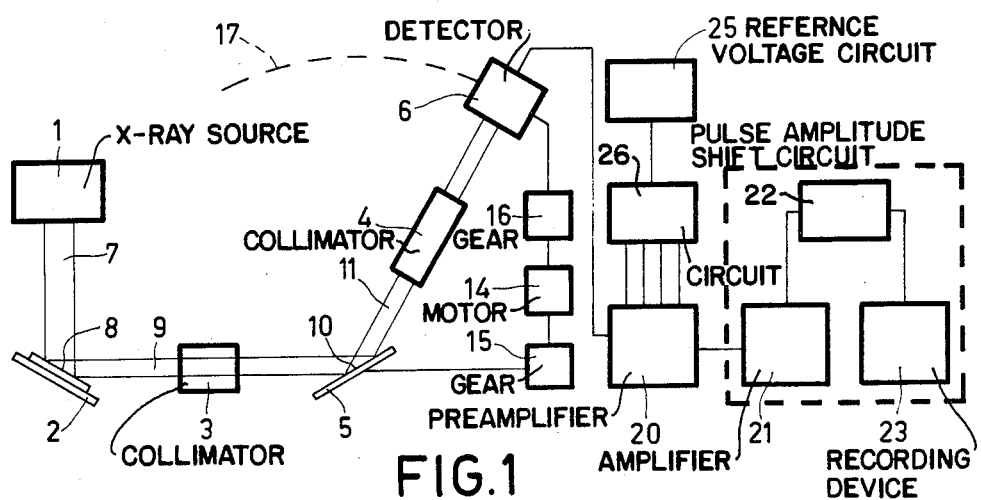
FIG. 1 shows very diagrammatically an X-ray analysis apparatus provided with a correction circuit according to the invention.

An X-ray analysis apparatus shown in FIG. 1 comprises an X-ray source 1, a sample holder 2, collimators 3 and 4, an analysing crystal 5 and a detector 6. An X-ray beam 7 strikes a test sample 8 and is there reflected in part. A reflected X-ray beam 9 incident via the collimator 3, on a surface 10 of the analysing crystal 5, after which a beam 11 reflected therefrom reaches the detector 6 via the collimator 4. A drive motor 14 acting via a transmission gear 15, causes the analysing crystal to rotate about an axis at right angles to the plane of the drawing. The motor 14 acting via a transmission gear 16, causes a rotation of the detector which matches the rotation of the crystal, likewise about an axis at right angles to the plane of the drawing. Due to this rotation, the detector is moved along an arc of a circle 17. The detector comprises, for example, a gas-filled detection cell, and measurement pulses which are generated therein by incident radiation quanta by ionisation, are applied to a pulse amplifier, which comprises a preamplifier 20 and a main amplifier 21. According to the invention, the amplifier has added to it a pulse amplitude shift correction circuit 22 to which is connected a recording device 23. Moreover, the preamplifier has connected to it a circuit element 26 which is connected to a reference voltage element 25 and in which by the adjustment of the apparatus given values for, for example the crystal type, the order of reflection, sine $\theta$ and the sensitivity adjustment, are formed.

Figure 2:
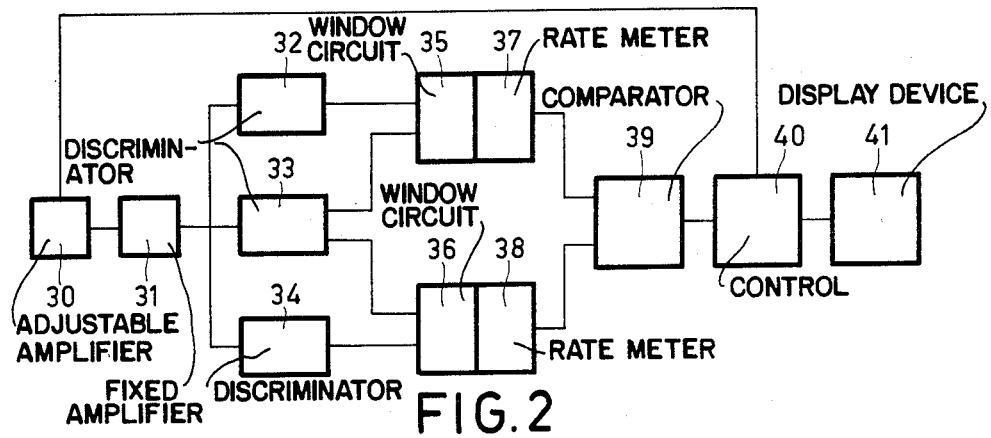
FIG. 2 shows a block circuit diagram of a correction circuit used therein.
Figure 3:
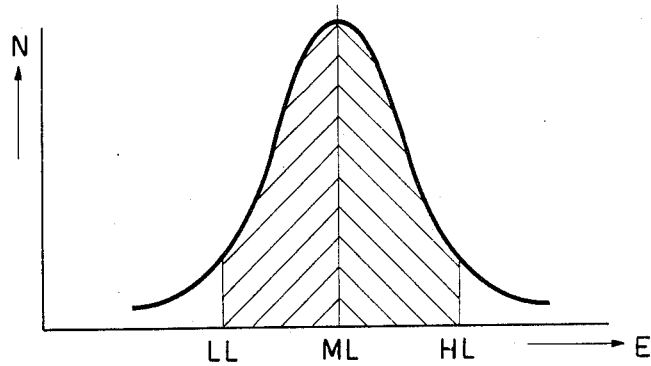
FIG. 3 shows an example of a pulse distribution to be measured.

FIG. 2 shows a more elaborate block circuit diagram of the detector reading system indicated in FIG. 1 within a frame of dotted lines. For the sake of clarity, the amplifier 21 is subdivided into an adjustable amplifier 30 and a fixed amplifier 31. The amplifier has connected to it in parallel arrangement three amplitude discriminators, i.e. a high threshold discriminator 32, an intermediate threshold discriminator 33 and a low threshold discriminator 34. Pulses accepted by the high threshold discriminator 32 are applied to an upper pass-range window circuit 35. Pulses accepted by the low threshold discriminator are passed on to a lower pass-range window circuit 36, while pulses accepted by the intermediate threshold discriminator are applied to both window circuits. The lower pass-range window circuit passes on only these pulses lying in an amplitude range between a low threshold level LL and an intermediate threshold level ML, whereas the upper pass-range window circuit passes on only those pulses lying between the intermediate threshold level ML and a high threshold level HL. This is outlined in FIG. 3, in which the number of pulses N is represented as a function of the pulse energy E. The amplitude pass-range window circuits further include rate meters 37 and 38, respectively. The rate meters form from the sequences of pulses passed by the respective window circuits, analogue voltage signals which are applied to a comparator circuit 39. In the comparator 39, the two voltage signals are compared with each other. When the two signals are unequal, a signal is formed which is a function of the occurring difference and this signal is applied to a control circuit 40. The amplification of the measurement pulses is thus adapted so that the center ML of the pulse distribution is shifted to a fixed position corresponding to the intermediate threshold level set by the intermediate threshold discriminator 33. Thus, by means of the feedback mechanism, an active form of amplification correction is achieved which results in the intermediate value of the pulse distribution being maintained at a point which is fixed but adjustable. When due to a pulse amplitude shift in the detector, for example in a form of gas-filled counting tube, the amplification decreases, this decrease will be compensated for in the amplifier so that the overall amplification will remain constant. The advantage of such an active control correction is that—irrespective of the type of counting tube or of the high voltage used—it invariably compensates to the optimum. The measured signals can be displayed and recorded on a display device 41.

What is claimed is:

1. In an X-ray apparatus comprising an X-ray source, a sample receiving X-rays from said source, an analyzing crystal receiving X-rays from said sample, and a detector receiving X-rays from said analyzing crystal, the improvement comprising said detector applying signals to amplifying means including a preamplifier for amplifying signals from said detector, circuit means for controlling said amplifying means, and means for recording and displaying said signals, wherein said circuit means includes a pulse amplitude shift correction circuit means for providing correction signals, said correction signals being a measure of and being in response to pulse amplitude shifts.

2. An X-ray apparatus according to claim 1, wherein said amplifying means includes an adjustable amplifier circuit and a fixed amplifier circuit, and wherein said pulse amplitude shift correction circuit means includes three parallel connected amplitude discriminators receiving signals from said amplifying means, two window circuits of different amplitude pass range values receiving output signals from said three discriminators, a comparator circuit having a memory and receiving further output signals from said two window circuits, and a control circuit receiving signals from said comparator circuit, said control circuit providing feedback signals to said adjustable amplifier.

3. An X-ray apparatus according to claim 2, wherein a rate meter is connected respectively to each of said window circuits for receiving pulses of said output signals, said rate meters passing said further output signal to said comparator circuit.

4. An X-ray apparatus according to claim 2, wherein said three discriminators provide respectively high threshold discrimination, intermediate threshold discrimination, and low threshold discrimination, and wherein one of said two window circuits receives output signals from said high threshold discriminator and said intermediate threshold discriminator, and another of said two window circuits receives output signals from said intermediate threshold discriminator and said low threshold discriminator.

* * * * *